United States Patent
Demos (10) Patent No.: US 10,182,708 B2
(45) Date of Patent: Jan. 22, 2019

(54) SIMULTANEOUS ACQUISITION OF DIFFERING IMAGE TYPES

(75) Inventor: Stavros G. Demos, Livermore, CA (US)

(73) Assignee: Lawrence Livermore National Security, LLC, Livermore, CA (US)

(*) Notice: Subject to any disclaimer, the term of this patent is extended or adjusted under 35 U.S.C. 154(b) by 633 days.

(21) Appl. No.: 13/601,918

(22) Filed: Aug. 31, 2012

(65) Prior Publication Data
US 2013/0033589 A1 Feb. 7, 2013

Related U.S. Application Data

(60) Division of application No. 12/167,104, filed on Jul. 2, 2008, now Pat. No. 8,285,015, which is a
(Continued)

(51) Int. Cl.
*A61B 1/04* (2006.01)
*A61B 1/06* (2006.01)
(Continued)

(52) U.S. Cl.
CPC .......... *A61B 1/043* (2013.01); *A61B 1/00009* (2013.01); *A61B 1/063* (2013.01);
(Continued)

(58) Field of Classification Search
CPC ... A61B 1/00009; A61B 1/043; A61B 1/0638; A61B 1/063; A61B 5/0075; A61B 5/0086; A61B 1/307; A61B 1/313
See application file for complete search history.

(56) References Cited

U.S. PATENT DOCUMENTS 3,116,417 A 12/1963 Orr et al.
3,750,046 A 7/1973 Buehler et al.
(Continued)

FOREIGN PATENT DOCUMENTS

EP 129364 A2 12/1984
EP 0352952 1/1990
(Continued)

OTHER PUBLICATIONS

Anutgan et al., "Effect of heat treatment on the stress and structure evolution of plasma deposited boron nitride thin films," Surface & Coatings Technology, vol. 202, 2008, pp. 3058-3066.
(Continued)

*Primary Examiner* — Mohammed Jebari
(74) *Attorney, Agent, or Firm* — Zilka-Kotab LLC (57) ABSTRACT

A system in one embodiment includes an image forming device for forming an image from an area of interest containing different image components; an illumination device for illuminating the area of interest with light containing multiple components; at least one light source coupled to the illumination device, the at least one light source providing light to the illumination device containing different components, each component having distinct spectral characteristics and relative intensity; an image analyzer coupled to the image forming device, the image analyzer decomposing the image formed by the image forming device into multiple component parts based on type of imaging; and multiple image capture devices, each image capture device receiving one of the component parts of the image. Additional systems and methods are presented.

24 Claims, 4 Drawing Sheets

Related U.S. Application Data continuation-in-part of application No. 11/796,689, filed on Apr. 27, 2007, which is a continuation of application No. 10/400,024, filed on Mar. 25, 2003, now Pat. No. 7,257,437, which is a continuation-in-part of application No. 10/190,231, filed on Jul. 5, 2002, now Pat. No. 7,016,717.

(60) Provisional application No. 60/958,557, filed on Jul. 6, 2007.

(51) Int. Cl.
    *A61B 1/313*     (2006.01)
    *A61B 5/00*     (2006.01)
    *A61B 1/00*     (2006.01)
    *A61B 1/307*     (2006.01)

(52) U.S. Cl.
    CPC ............ *A61B 1/0638* (2013.01); *A61B 1/307* (2013.01); *A61B 5/0075* (2013.01); *A61B 5/0086* (2013.01); *A61B 1/313* (2013.01)

(56) References Cited

U.S. PATENT DOCUMENTS

| | | | |
|---|---|---|---|
| 3,817,633 A | | 6/1974 | White |
| 3,988,586 A | | 10/1976 | Stuart et al. |
| 4,127,499 A | | 11/1978 | Chen et al. |
| 4,482,808 A | | 11/1984 | Tominaga et al. |
| 4,692,266 A | | 9/1987 | Costa et al. |
| 4,718,417 A | * | 1/1988 | Kittrell et al. .................. 606/7 |
| 4,803,992 A | * | 2/1989 | Lemelson .......... A61B 1/00096 |
| | | | 600/342 |
| 4,930,516 A | | 6/1990 | Alfano et al. |
| 4,957,114 A | | 9/1990 | Zeng et al. |
| 4,957,117 A | | 9/1990 | Wysham |
| 4,974,076 A | * | 11/1990 | Nakamura ............... A61B 1/05 |
| | | | 348/71 |
| 5,042,494 A | | 8/1991 | Alfano |
| 5,131,398 A | | 7/1992 | Alfano et al. |
| 5,261,410 A | | 11/1993 | Alfano et al. |
| 5,313,306 A | | 5/1994 | Kuban et al. |
| 5,348,018 A | | 9/1994 | Alfano et al. |
| 5,436,655 A | * | 7/1995 | Hiyama et al. ................. 348/45 |
| 5,467,767 A | | 11/1995 | Alfano et al. |
| 5,593,879 A | | 1/1997 | Steller et al. |
| 5,606,638 A | | 2/1997 | Tymianski et al. |
| 5,726,453 A | | 3/1998 | Lott et al. |
| 5,749,830 A | * | 5/1998 | Kaneko .............. A61B 1/00082 |
| | | | 348/E5.038 |
| 5,769,081 A | | 6/1998 | Alfano et al. |
| 5,833,596 A | | 11/1998 | Bonnell et al. |
| 5,847,394 A | | 12/1998 | Alfano et al. |
| 5,872,363 A | | 2/1999 | Bingham et al. |
| 5,940,460 A | | 8/1999 | Seidel et al. |
| 5,976,076 A | | 11/1999 | Kolff et al. |
| 5,997,472 A | | 12/1999 | Bonnell et al. |
| 6,009,340 A | | 12/1999 | Hsia |
| 6,061,591 A | * | 5/2000 | Freitag et al. ................ 600/476 |
| 6,169,289 B1 | | 1/2001 | White et al. |
| 6,269,169 B1 | | 7/2001 | Funk et al. |
| 6,413,267 B1 | | 7/2002 | Dumoulin-White et al. |
| 6,462,770 B1 | | 10/2002 | Cline et al. |
| 6,477,403 B1 | | 11/2002 | Eguchi et al. |
| 6,529,769 B2 | | 3/2003 | Zigler |
| 6,544,442 B1 | | 4/2003 | Bell et al. |
| 6,598,428 B1 | | 7/2003 | Cryan et al. |
| 6,687,000 B1 | | 2/2004 | White |
| 6,730,019 B2 | | 5/2004 | Irion |
| 6,775,567 B2 | | 8/2004 | Cable et al. |
| 6,949,069 B2 | | 9/2005 | Farkas et al. |
| 6,975,898 B2 | | 12/2005 | Seibel |
| 6,975,899 B2 | | 12/2005 | Faupel et al. |
| 7,003,147 B2 | | 2/2006 | Inoue |
| 7,016,717 B2 | | 3/2006 | Demos et al. |
| 7,067,079 B2 | | 6/2006 | Bross et al. |
| 7,145,149 B2 | | 12/2006 | Cooke et al. |
| 7,164,138 B2 | | 1/2007 | McGregor et al. |
| 7,172,553 B2 | | 2/2007 | Ueno et al. |
| 7,257,437 B2 | | 8/2007 | Demos et al. |
| 7,372,041 B1 | | 5/2008 | Nagarkar et al. |
| 7,723,114 B1 | | 5/2010 | Coates, Jr. et al. |
| 7,930,516 B1 | | 4/2011 | Jin et al. |
| 7,945,077 B2 | | 5/2011 | Demos |
| 8,207,507 B2 | | 6/2012 | Zaitseva et al. |
| 8,285,015 B2 | | 10/2012 | Demos |
| 8,461,546 B2 | | 6/2013 | Payne et al. |
| 8,580,054 B2 | | 11/2013 | Pagoria et al. |
| 8,735,843 B2 | | 5/2014 | Payne et al. |
| 2001/0030744 A1 | | 10/2001 | Chang |
| 2001/0056238 A1 | * | 12/2001 | Tsujita ........................ 600/476 |
| 2002/0103439 A1 | * | 8/2002 | Zeng et al. .................... 600/476 |
| 2003/0007087 A1 | * | 1/2003 | Hakamata ............ A61B 1/0638 |
| | | | 348/370 |
| 2003/0078477 A1 | * | 4/2003 | Kang ...................... A61B 1/042 |
| | | | 600/178 |
| 2003/0158470 A1 | | 8/2003 | Wolters et al. |
| 2003/0222198 A1 | * | 12/2003 | Olszak ............... G02B 21/0004 |
| | | | 250/208.1 |
| 2003/0232445 A1 | | 12/2003 | Fulghum |
| 2004/0019281 A1 | * | 1/2004 | Weber et al. ................. 600/476 |
| 2004/0109231 A1 | * | 6/2004 | Haisch et al. ................. 359/385 |
| 2004/0245350 A1 | * | 12/2004 | Zeng ............................. 236/43 |
| 2005/0020926 A1 | | 1/2005 | Wiklof et al. |
| 2006/0054863 A1 | | 3/2006 | Dai et al. |
| 2006/0086311 A1 | | 4/2006 | Zagumennyi et al. |
| 2007/0175383 A1 | | 8/2007 | Fukuda et al. |
| 2008/0004495 A1 | * | 1/2008 | Allen ..................... A61B 1/043 |
| | | | 600/160 |
| 2008/0017804 A1 | | 1/2008 | Krishnamoorthy et al. |
| 2008/0267472 A1 | | 10/2008 | Demos |
| 2010/0256923 A1 | | 10/2010 | Payne et al. |
| 2011/0266643 A1 | | 11/2011 | Engelmann et al. |
| 2011/0284755 A1 | | 11/2011 | Stradins et al. |
| 2012/0241630 A1 | | 9/2012 | Walker et al. |
| 2012/0326042 A1 | | 12/2012 | Zaitseva et al. |
| 2013/0181135 A1 | | 7/2013 | Payne et al. |
| 2013/0187056 A1 | | 7/2013 | Nikolic et al. |
| 2013/0299702 A1 | | 11/2013 | Zaitseva et al. |

FOREIGN PATENT DOCUMENTS

| | | | | |
|---|---|---|---|---|
| GB | 2254417 A | * | 10/1992 | ............ G01N 21/64 |
| WO | 9605693 A1 | | 2/1996 | |
| WO | WO 9605693 A1 | * | 2/1996 | ........... A61B 1/0638 |
| WO | 0238040 A2 | | 5/2002 | |
| WO | WO2012142365 | | 10/2012 | |

OTHER PUBLICATIONS

Dusane, R. O., "Opportunities for new materials synthesis by hot wire chemical vapor process," Thin Solid Films, vol. 519, 2011, pp. 4555-4560.

Lattemann et al., "New approach in depositing thick, layered cubic boron nitride coatings by oxygen addition—structural and compositional analysis," Thin Solid Films, vol. 515, 2006, pp. 1058-1062.

Bello et al., "Deposition of thick cubic boron nitride films: The route to practical applications," Diamond & Related Materials, vol. 14, 2005, pp. 1154-1162.

He et al., "Improvement of adhesion of cubic boron nitride filsm: effect of interlayer and deposition parameters," Materials Science Forum, vols. 475-479, 2005, pp. 3637-3638.

Shultis et al., "Efficiencies of Coated and Perforated Semiconductor Neutron Detectors," 2004 IEEE, pp. 4569-4574.

McGregor et al., "New Surface Morphology for Low Stress Thin-Film-Coated Thermal Neutron Detectors," 2002 IEEE, IEEE Transactions on Nuclear Science, vol. 49, No. 4, Aug. 2002, pp. 1999-2004.

Matsumoto et al., "The introducing of fluorine into the deposition of BN: a successful method to obtain high-quality, thick cBN films (56) References Cited

OTHER PUBLICATIONS with low residual stress," Diamond and Related Materials, vol. 10, 2001, pp. 1868-1874.
Karim et al., "Effect of deposition parameters on the formation of cubic BN films deposited by plasma-assisted chemical vapour deposition from non-toxic material," Surface and Coatings Technology, vol. 54-55, 1992, pp. 355-359.
U.S. Appl. No. 13/742,298, filed Jan. 15, 2013.
U.S. Appl. No. 13/471,259, filed May 14, 2012.
U.S. Appl. No. 13/437,836, filed Apr. 2, 2012.
U.S. Appl. No. 13/439,780, filed Apr. 4, 2012.
Final Office Action from U.S. Appl. No. 13/437,836 dated May 22, 2014.
Notice of Allowance and Fee(s) Due from U.S. Appl. No. 13/477,910 dated Apr. 16, 2014.
Peurrung, A. J., "Recent developments in neutron detection," 2000 Elsevier Science B.V., Nuclear Instruments and Methods in Physics Research A, vol. 443, 2000, pp. 400-415.
Brooks, F. D., "Development of Organic Scintillators," North-Holland Publishing Co., Nuclear Instruments and Methods, vol. 162, 1979, pp. 477-505.
Vijayan et al., "Growth, optical, thermal and mechanical studies of methyl 4-hydroxybenzoate single crystals," 2003 Elsevier B.V., Journal of Crystal Growth, vol. 256, 2003, pp. 174-182.
Varfolomeeva, V. N., et al., "Polarization Diagrams for the Fluorescence of Single Crystals of Salicylic Acid and Salicylates," Soviet Physics—Crystallography, vol. 13, No. 2, Sep.-Oct. 1968, pp. 209-211.
Mandshukov, I. G., et al., "Properties of a New Class of Organic Scintillators: Derivatives of Salicyclic Acid," 1982 Plenum Publishing Corporation, University of Sofia, Bulgaria, Translated from Pribory i Tekhnika Eksperimenta, No. 3, May-Jun. 1981, pp. 605-611.
Zhao et al., "Characteristics of large-sized Ce:YAG Scintillation crystal grown by temperature gradient technique," 2003 Elsevier B.V., Journal of Crystal Growth, vol. 253, 2003, pp. 290-296.
Non-Final Office Action from U.S. Appl. No. 12/418,434 dated May 20, 2011.
Non-Final Office Action from U.S. Appl. No. 12/418,434 dated Nov. 22, 2011.
Notice of Allowance and Fee(s) Due from U.S. Appl. No. 12/418,434 dated Feb. 23, 2012.
Non-Final Office Action from U.S. Appl. No. 12/418,450 dated Jul. 13, 2011.
Non-Final Office Action from U.S. Appl. No. 12/418,450 dated Nov. 15, 2011.
Final Office Action from U.S. Appl. No. 12/418,450 dated Feb. 24, 2012.
Notice of Allowance and Fee(s) Due from U.S. Appl. No. 12/418,450 dated Oct. 22, 2012.
Non-Final Office Action from U.S. Appl. No. 13/736,898 dated Mar. 8, 2013.
Non-Final Office Action from U.S. Appl. No. 12/418,450 dated Jun. 14, 2012.
Final Office Action from U.S. Appl. No. 13/736,898 dated Jun. 24, 2013.
Final Office Action from U.S. Appl. No. 12/167,104 dated Feb. 23, 2012.
Restriction/Election Requirement from U.S. Appl. No. 12/167,104 dated Jun. 8, 2011.
Non-Final Office Action from U.S. Appl. No. 12/167,104 dated Sep. 15, 2011.
Notice of Allowance and Fee(s) Due from U.S. Appl. No. 12/167,104 dated Jun. 21, 2012.
Non-Final Office Action from U.S. Appl. No. 13/437,836 dated Nov. 7, 2013.
Notice of Allowance and Fee(s) Due from U.S. Appl. No. 13/736,898 dated Jan. 13, 2014.
Advisory Action from U.S. Appl. No. 13/736,898 dated Dec. 9, 2013.
Notice of Allowance and Fee(s) Due from U.S. Appl. No. 13/439,780 dated Jun. 12, 2013.
Restriction/Election Requirement from U.S. Appl. No. 13/439,780 dated Mar. 28, 2013.
Notice of Allowance and Fee(s) Due from U.S. Appl. No. 13/439,780 dated Jul. 31, 2013.
Udagawa et al., "Aberrant Porphyrin Metabolism in Hepatocellular Carcinoma," 1984 Academic Press, Inc., Biochemical Medicine, vol. 31, pp. 131-139.
Pitts et al., "Autofluorescene characteristics of immortalized and carcinogen-transformed human bronchial epithelial cells," 2001 SPIE, Journal of Biomedical Optics, vol. 6, No. 1, Jan. 2001, pp. 31-40.
Zawirska, B., "Comparative Porphyrin Content in Tumors with Contiguous Non-Neoplastic Tissues," 1979, Neoplasma, vol. 26, No. 2, pp. 223-229.
Malik et al., "Destruction of Erythroleukaemic Cells by Photoactivation of Endogenous Porphyrins," The Macmillan Press Ltd., 1987, Br. J. Cancer, 1987, vol. 56, pp. 589-595.
Zhang et al., "Far-red and NIR Spectral Wing Emission from Tissues under 532 and 632 nm Photo-excitation," 1999 OPA, Lasers in the Life Sciences, vol. 9, pp. 1-16.
Alfano et al., "Laser Induced Fluorescence Spectroscopy from Native Cancerous and Normal Tissue," 1984 IEEE, IEEE Journal of Quantum Electronics, vol. QE-20, No. 12, Dec. 1984, pp. 1507-1511.
Navone et al., "Heme Biosynthesis in Human Breast Cancer-Mimetic "In Vitro" Studies and Some Heme Enzymic Activity Levels," 1990 Pergamon Press Pic, International Journal on Biochemistry, vol. 22, No. 12, pp. 1407-1411
Richards-Kortum et al., "Spectroscopic Diagnosis of Colonic Dysplasia," 1991 Pergamon Press Pic, Photochemistry and Photobiology, vol. 53, No. 6, pp. 777-786.
Demos et al., "Subsurface Imaging Using the Spectral Polarization Difference Technique and NIR Illumination," Part of the SPIE Conference on Optical Tomography and Spectroscopy of Tissue III, Jan. 1991, SPIE 3597, pp. 406-410.
Demos et al., "Tissue Imaging for Cancer Detection Using Nir Autofluorescence," 2002 SPIE, Optical Biopsy IV, Proceedings of SPIE, vol. 4613, pp. 31-34.
Corle et al., "Chapter 2—Instruments," Confocal Scanning Optical Microscopy and Related Imaging Systems, 1996, pp. 67-145.
Andrianov et al., "Synthesis and Properties of 4-Amino-3-Cyanofurazan," 1994 Plenum Publishing Corporation, Chemistry of Heterocyclic Compounds, vol. 30, No. 5, 1994, pp. 608-611.
Yarovenko et al., "15N NMR study of the mechanism of the reaction of amidoximes with nitriles in the presence of ZnCl2 and HCl," 1995 Plenum Publishing Corporation, Russian Chemical Bulletin, vol. 43, No. 4, Apr. 1994, pp. 627-629.
Yarovenko et al., "A convenient synthesis of 3-substituted 5-guanidino-1, 2, 4-Oxadiazoles," 1994 Plenum Publishing Corporation, Russian Chemical Bulletin, vol. 43, No. 1, Jan. 1994, pp. 114-117.
Yarovenko et al., "Synthesis of 2-amino-5-(5R-1,2,4-Oxadiazolyl-3)-1,3,4-Oxadiazoles," 1994 Plenum Publishing Corporation, Russian Chemical Bulletin, vol. 42, No. 12, Dec. 1993, pp. 2014-2017.
Yarovenko et al., "New Synthesis of 1,2,4-Oxadiazoles," Tetrahedron, vol. 46, No. 11, 1990, pp. 3941-3952.
Wang et al., "Morphological instability of crystals grown from thin aqueous solution films with a free surface," 1995 Taylor & Francis Ltd., Philosophical Magazine A, 1995, vol. 71, No. 2, pp. 409-419.
Bryan et al., "Fast Neutron-Gamma Pulse Shape Discrimination of Liquid Scintillation Signals for Time Correlated Measurements," Nuclear Science Symposium Conference Record, 2003 IEEE, Oct. 19-25, 2003, vol. 2, pp. 1192-1195.
Soderstrom, P., "Pulse Shape Discrimination Between Neutrons and Gamma Rays with Digital Electronics," Nuclear Structure Group, Department of Nuclear and Particle Physics, Uppsala University.
Jhingan et al, "Simple Ways of n-y Discrimination Using Charge Comparison Technique," ScienceDirect, Nuclear Instruments and Methods in Physics Research A 585 (2008) 165-171.
Soderstrom, P. et al, "Digital Pulse-Shape Discrimination of Fast Neutrons and y Rays," ScienceDirect, Nuclear Instruments and Methods in Physics Research A 594 (2008) 79-89.

(56) References Cited

OTHER PUBLICATIONS

Lawrence Livermore National Laboratory, "Laboratory Directed Research and Development, FY2007 Annual Report."
Greenwood et al., "Li-Salicylate Neutron Detectors with Pulse Shape Discrimination," Nuclear Instruments and Methods 165 (1979) 129-131.
Sangster et al., "Study of Organic Scintillators," The Journal of Chemical Physics, vol. 24, No. 4, Apr. 1956, pp. 670-715.
Sellin et al., "Digital Pulse Shape Discrimination Applied to Capture-Gated Neutron Detectors," Department of Physics, University of Surrey, Guildford, UK, 2008, pp. 1-18.
Zaitseva et al., "Neutron detection with single crystal organic scintillators," SPIE Hard X-Ray, Gamma-Ray, and Neutron Detector Physics, Lawrence Livermore National Laboratory, Jul. 20, 2009, pp. 1-10.
Bell et al., "Gadolinium- and Boron-Loaded Organic Scintillators for Neutron Detection," Transactions of the American Nuclear Society, vol. 83, 2000, pp. 259-260.
Carturan et al., "Novel Polysiloxane-Based Scintillators for Neutron Detection," Radiation Protection Dosimetry, vol. 143, No. 2-4, 2011, pp. 471-476.
Koshimizu et al., "Organic-Inorganic Hybrid Scintillator for Neutron Detection Fabricated by Sol-Gel Method," Japanese Journal of Applied Physics, vol. 47, No. 7, 2008, pp. 5717-5719.
Brown et al., "Applications of Nanoparticles in Scintillation Detectors," Antiterrorism and Homeland Defence: Polymers and Materials, American Chemical Society, vol. 980, 2008, pp. 117-129.
Kim et al., "Performance of Hybrid Plastic Scintillator Detectors for Low-Energy Neutron Measurements," Journal of the Korean Physical Society, vol. 52, No. 3, Mar. 2008, pp. 908-912.
Normand et al., "Discrimination methods between neutron and gamma rays for boron loaded plastic scintillators," Nuclear Instruments & Methods in Physics Research A, vol. 484, 2002, pp. 342-350.
Quaranta et al., "Optical and Scintillation Properties of Polydimethyl-Diphenylsiloxane Based Organic Scintillators," IEEE Transactions on Nuclear Science, vol. 57, No. 2, Apr. 2010, pp. 891-900.
Quaranta et al., "Doping of polysiloxane rubbers for the production of organic scintillators," Optical Materials, vol. 32, No. 10, 2010, pp. 1317-1320.
Hull et al., "New Organic Crystals for Pulse Shape Discrimination," IEEE Transactions on Nuclear Science, vol. 56, No. 3, Jun. 2009, pp. 899-903.
Iwanowska et al., "Composite Scintillators as Detectors for Fast Neutrons and Gamma-Radiation Detection in the Border Monitoring," 2009 IEEE Nuclear Science Symposium Conference Record, pp. 1437-1440.
Hamel et al., "Fluorescent 1,8-naphthalimides-containing polymers as plastic scintillators. An attempt for neutron-gamma discrimination," Reactive & Functional Polymers, vol. 68, No. 12, 2008, pp. 1671-1681.
Kim et al., "Characteristics of Hybrid Plastic Scintillators for Slow Neutron Measurements," 2007 IEEE Nuclear Science Symposium Conference Record, pp. 1971-1975.
Katagiri et al., "Scintillation materials for neutron imaging detectors," Nuclear Instruments & Methods in Physics Research A, vol. 529, 2004, pp. 274-279.
Gervino et al., "A low background, large solid angle neutron detector for spectroscopy and dosimetry application." Sensors and Actuators A, vol. 41-42, 1994, pp. 497-502.
Kubota et al., "A New Solid State Neutron Detector: Particle Identification With a Barium-Fluoride Plastic Scintillator." Nuclear Instruments & Methods in Physics Research, vol. A270, 1998, pp. 598-601.
Shaposhnikov et al., "New Heterocycles with a 3-Aminofurazanyl Substituent," 2002 MAIK, Russian Journal of Organic Chemistry, vol. 38, No. 9, 2002, pp. 1351-1355.
Demos, S.G., U.S. Appl. No. 12/167,104, filed Jul. 2, 2008.
Schomacker et al., "Ultraviolet Laser-Induced Fluorescence of Colonic Tissue: Basic Biology and Diagnostic Potential," Lasers in Surgery and Medicine 12, 1992, pp. 63-78.
Demos, S.G., U.S. Appl. No. 11/292,406, filed Nov. 30, 2005.

* cited by examiner

SIMULTANEOUS ACQUISITION OF DIFFERING IMAGE TYPES

RELATED APPLICATIONS

This application is a divisional of U.S. Pat. No. 8,285,015 filed on Jul. 2, 2008, which claims priority to provisional U.S. application No. 60/958,557 filed on Jul. 6, 2007; and which is also a continuation-in-part of U.S. application Ser. No. 11/796,689 filed on Apr. 27, 2007, which is a continuation of U.S. Pat. No. 7,257,437 filed on Mar. 25, 2003 which is a continuation-in-part of U.S. Pat. No. 7,016,717 filed Jul. 5, 2002; priority of each of which is hereby claimed, and each of which is herein incorporated by reference.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to image acquisition, and more particularly to simultaneous formation, transfer, decomposition and/or capture of multi-spectral and or multi-modal images.

BACKGROUND

While visual examination still remains the most important diagnostic method, recent rapid progress in photonic technologies for real time pathological assessment has demonstrated a great deal of promise by expanding the dimension and spectral range of observation. The spatial resolution of these new technologies extends from the tissue to the single cell level and can provide information in real time to help enhance the ability of a surgeon to determine the status of tissue. Development of technology capable of providing diagnostic information in real time could revolutionize a number of diagnostic and therapeutic clinical procedures.

Optical biopsy utilizes optical spectroscopy techniques to characterize tissue, and requires direct exposure of the tissue under examination to the light source. It is therefore particularly suitable in a clinical setting for intraoperative use to assist in the assessment of the tissue in real time. Numerous reports over the past 20 years have highlighted a number of spectroscopic approaches capable of detecting cancer and separating out the different tissue components. An example of such a technology is described in U.S. application Ser. No. 10/400,024 filed on Mar. 25, 2003, from which priority is claimed.

Tissue characterization via photonic techniques explores the use of intrinsic optical signatures (contrast mechanisms) or extrinsic contrast agents to detect and/or image abnormal (such as cancer) tissues and organs in real time. Although basic research has provided the proof of concept that a number of different approaches can provide histopathology information in real time, to date there has been limited success in translating this photonic technology into novel medical instrumentation. Arguably, this may be yet another example of a new technology that industry fails to recognize its potential in a timely fashion or a failure by scientists to design and build instrumentation suitable for use in a clinical setting that has the potential to emerge from the basic research level.

SUMMARY

A system in one embodiment includes an image forming device for forming an image from an area of interest containing different image components; an illumination device for illuminating the area of interest with light containing multiple components; at least one light source coupled to the illumination device, the at least one light source providing light to the illumination device containing different components, each component having distinct spectral characteristics and relative intensity; an image analyzer coupled to the image forming device, the image analyzer decomposing the image formed by the image forming device into multiple component parts based on type of imaging; and multiple image capture devices, each image capture device receiving one of the component parts of the image.

A system in one embodiment includes an image analyzer for coupling to an image forming device adapted for insertion in a human body, the image analyzer decomposing an image formed by the image forming device into multiple component parts based on type of imaging; multiple image capture devices, each image capture device receiving one of the component parts of the image; and a processing device coupled to the image capture devices.

A method in one embodiment includes receiving an image from an image forming device; decomposing the image formed by the image forming device into multiple component parts based on type of imaging; receiving the component parts of the image; and outputting image information based on the component parts of the image.

Other aspects and embodiments of the present invention will become apparent from the following detailed description, which, when taken in conjunction with the drawings, illustrate by way of example the principles of the invention.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

A system in one general embodiment includes an image forming device for forming an image from an area of interest containing different image components; an illumination device for illuminating the area of interest with light containing multiple components; at least one light source coupled to the illumination device, the at least one light source providing light to the illumination device containing different components, each component having distinct spectral characteristics and relative intensity; an image analyzer coupled to the image forming device, the image analyzer decomposing the image formed by the image forming device into multiple component parts based on type of imaging; and multiple image capture devices, each image capture device receiving one of the component parts of the image.

A system in one general embodiment includes an image analyzer for coupling to an image forming device adapted for insertion in a human body, the image analyzer decomposing an image formed by the image forming device into multiple component parts based on type of imaging; multiple image capture devices, each image capture device receiving one of the component parts of the image; and a processing device coupled to the image capture devices.

A method in one general embodiment includes receiving an image from an image forming device; decomposing the image formed by the image forming device into multiple component parts based on type of imaging; receiving the component parts of the image; and outputting image information based on the component parts of the image.

Instrumentation is described according to various embodiments that can be adapted to any type of image forming device (e.g., camera lenses, microscope lens, etc) of image forming and relaying devices (e.g. endoscopes, laparoscopes, boroscopes, endoscope-type devices used in the medical field to view interior body structures, etc.) that offers the ability to simultaneously acquire multiple optical images that are based on different methodologies. This may include simultaneous acquisition of two or more of the following (or other) types of images: conventional color (RGB) image, auto fluorescence images, image based on fluorescence of a contrast agent, polarization sensitive image, light scattering images at different spectral ranges, Raman scattering spectrum from a localized area, etc. In some approaches, the images can be acquired through a wide range of spatial resolutions. Moreover, imaging can be performed from the micro scale (e.g., cell level) to the macro scale (e.g., tissue level), and anywhere in between. Some embodiments also allow transitioning from one scale to another.

According to various embodiments, the instrumentation may be particularly suitable for medical applications when adapted to various types of endoscopic devices such as, e.g., colonoscopes, cystoscopes, laparoscopes, bronchoscopes, etc., to examine interior body organs and tissues using multiple optical spectroscopy-based imaging techniques while the conventional color image is simultaneously recorded so that several or all of the images can be displayed in real time. The benefit of such application is that the visual examination, which still remains the most important diagnostic method during surgery, is complemented by the spectral image(s) which can provide additional diagnostic information in the most efficient manner that allows for easy co-registration and correlation of image features and minimized acquisition time.

In one particularly preferred approach, novel instrumentation for tissue diagnosis provides expedited information and high sensitivity and specificity. One important parameter to be taken into account is the limited time a patient can spend in the operating room. This weighs heavily in favor of instrumentation that offers fast scanning speed. Consequently, in one approach, the main screening technique may be of low spatial resolution but at the same time, may provide high sensitivity. In other embodiments, an important issue is to be able to accurately assess the margins of a tumor. Margin delineation may require higher spatial resolution and also higher specificity. Several multimodal approaches presented herein incorporate high sensitivity and specificity. Moreover, the new technologies presented herein may be complementary to existing methodologies.

In various embodiments, the task of achieving integration of imaging methodologies (conventional and novel spectroscopic) includes acquiring all images simultaneously by the same image forming device (lens, endoscope, etc). Accordingly, one embodiment of the present invention includes instrumentation that can integrate acquisition in real time of color conventional imaging with spectral imaging or point spectroscopic measurements over a wide range of spatial resolutions. This instrumentation can preferably be adapted to any existing image forming device such as those already in use in the medical field. Furthermore, the design of such instrumentation may take into consideration the surgeon's work ergonomy. It is generally desirable that the tools used by the surgeon are lightweight and have physical dimensions compatible with the human anatomy.

While much of the following discussion focuses on the detection of cancer, this is done by way of example only. It should therefore be kept in mind that the same type of technology can be used to image and/or separate out various components in other types of tissue such as nerves, veins, arteries, tumors, scar tissue, foreign objects such as shrapnel, etc. Furthermore, it can be used to evaluate tissue components exposed to various adverse conditions such as ischemic or chemical injury and genetic defects. Other uses and applications are also anticipated.

One clinical setting particularly pertinent to the teachings herein is the detection and imaging of cancer located inside the body via endoscopes. Based on the discussion above, the design of an endoscopic system for real time cancer detection and margin delineation preferably affords fast screening speed, and the ability to examine the margins with high spatial resolution and high sensitivity and specificity. To achieve fast screening speed, one embodiment employs macroscopic dual imaging where a conventional color (red/green/blue, or RGB) or black and white image is displayed simultaneously with the spectral image to help determine abnormal tissue regions.

Any type of conventional color or black and white imaging technology can be used. Illustrative components are presented below.

The spectral image may be based on other types of imaging, such as auto fluorescence images, image based on fluorescence of a contrast agent, polarization sensitive image, light scattering images at different spectral ranges, Raman scattering spectrum from a localized area, etc. For example, optical biopsy utilizes optical spectroscopy techniques to characterize tissue, and requires direct exposure of the tissue under examination to the light source. It is therefore particularly suitable in a clinical setting for intraoperative use to assist in the assessment of the tissue in real time.

The spectral image may also be based on a wide range of photonic techniques. Tissue characterization via photonic techniques explores the use of intrinsic optical signatures (contrast mechanisms) or extrinsic contrast agents to detect and/or image abnormal (such as cancer) tissues and organs in real time.

The spectral image may be based on the utilization of the Near Infrared (NIR) Autofluorescence under long-wavelength excitation imaging technique in combination with NIR light scattering as described in U.S. Pat. No. 7,257,437 to Stavros et al., which is herein incorporated by reference.

Figure 1:
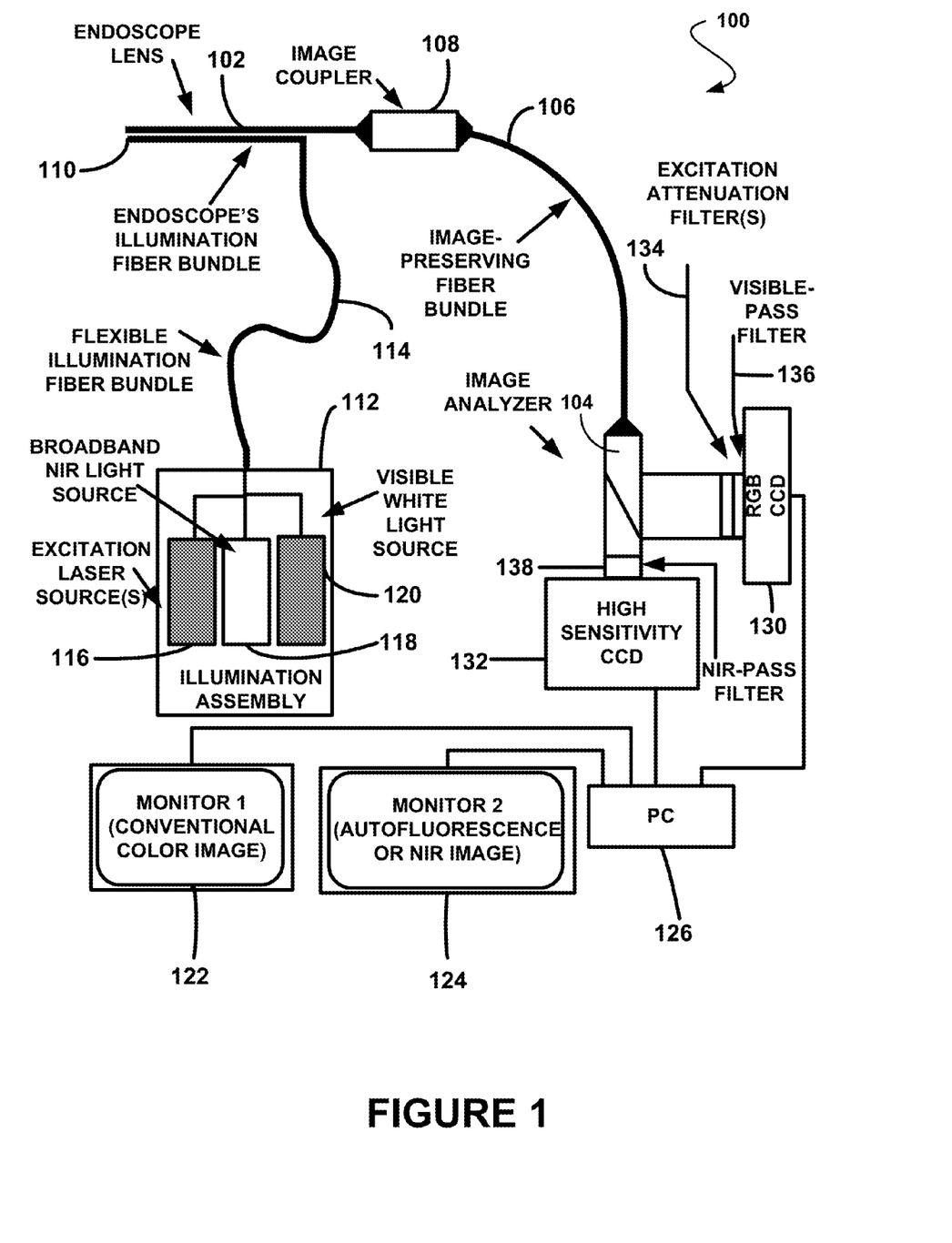
FIG. 1 illustrates a system for simultaneous acquisition of images using different techniques according to one embodiment.

FIG. 1 is a schematic diagram of an imaging system 100 according to one embodiment. As shown in FIG. 1, the system 100 includes an image forming device 102. The image forming device 102 used to form, and optionally relay, an image from the area of interest (e.g., tissue or internal organ) can be or include any conventional device such as camera lenses, various types of endoscopes designed to achieve direct visualization of objects located in a remote location, or other modality. Therefore, one embodiment of the system design presented here can be adapted to any existing image forming instrumentation already available at a user location.

An image transfer line 106, such as an image preserving fiber or fiber bundle, a conduit or channel having reflective portions, e.g., mirrors, etc., relays the image from the image forming device 102 to a separate location where the image can be retrieved, decomposed into individual components or modified via optical mechanisms. The resulting image information based on the capture device output, including raw or processed image data, can thereafter be directly displayed on the same or on separate output devices 122, 124 such as video monitors or other types of display devices, and/or further processed using appropriate computer software e.g., on a processing device 126, e.g., computer, chip, Application Specific Integrated Circuit (ASIC), etc., for output of information derived therefrom. Accordingly, as implied, each output device may display information corresponding to one or more of the component parts of the image. Moreover, images can be "fused" into composite images via software and/or hardware and output on one or more of the monitors 122, 124. In one approach, an NIR image is superimposed on a color image. The overlying image may be translucent, semitransparent, and/or nontranslucent. Further, the overlying image may include only portions of the source image, such as portions having a contrast or intensity in some range, or above or below a threshold value.

An illumination device 110 may be coupled to the image forming device 102. In one approach, an illumination channel of the endoscope 102 or other image forming device may be used to carry the illumination light from an illumination assembly 112 to the remote location to be imaged. The illumination device 110 may be integral to the image forming device 102, or coupled thereto. The illumination device 110 can also be free from the image forming device 102. In one approach, the illumination device 110 includes a fiber or fiber bundle that is part of the image forming device 102. Light from an illumination assembly 112 is carried to the illumination device 110 by appropriate transfer mechanism 114, such as a fiber or fiber bundle. The transfer mechanism 114 is preferably flexible. The illumination assembly 112 may include one or more light sources 116, 118, 120, as needed to illuminate the sample (organ, tissue, etc.) being imaged in the appropriate format. The light source(s) provide light to the illumination device containing different components, each component having distinct spectral characteristics and relative intensity. Illustrative light sources include broadband or narrow band NIR light sources, excitation laser sources, visible light sources, monochromatic light sources, other narrow band light sources, ultraviolet light sources, etc. For example, NIR spectral imaging may be based on light scattering from tissue, tissue autofluorescence, emission by a fluorescent contrast agent, etc.

In the illustrative embodiment of FIG. 1, the illumination includes a white light source 120 covering the visible spectrum to facilitate the acquisition of the conventional color image. In addition, laser sources 116, 118 are used to excite the tissue or a contrast agent (e.g., that has been applied to the tissue area to be imaged through topical application, the vascular system or other method) at the desired wavelength to produce the fluorescence signal to be used to form the spectral image.

In various approaches, the illumination light sources 116, 118, 120 may be coupled to the illumination channel that may already exist in the image relaying device 102. In the case of endoscopes, an illumination fiber is used to deliver light into the interior body location to be imaged. This same illumination channel can be used to deliver the output of the system's light sources into the location to be imaged.

Note that the image forming device 102 may be coupled directly to the image transfer line 106. Alternatively, the image formed by image forming device 102 may be coupled to the image transfer line 106 via the use of an image coupler 106 which is comprised mainly of a set of lenses to relay the image from the image forming device 102 to the image transfer line 106.

In other approaches, an optional image transfer module 108 may interface with the image forming device 102 to assist in coupling the formed image to the image transfer line 106. The image transfer line 106 is preferably flexible, or preferably has a flexible section to allow articulation of the image forming device 102. One vendor of fiber optic bundles that may be used in various embodiments is Schott Fiber Optics, Inc., d.b.a. SCHOTT North America, Inc., 555 Taxter Road, Elmsford, N.Y. 10523, USA. Types of fibers and fiber bundles that are usable with some embodiments are presented in U.S. Pat. No. 6,598,428 to Cryan et al., which is herein incorporated by reference for its teaching of fibers and fiber bundles.

In use, the image is retrieved at the distal end of the image transport line 106 using appropriate optics 108 and projected towards an image analyzer 104 that splits the image into component parts, which are directed towards two or more different image recording devices 130, 132, e.g., cameras, after being split. The image analyzer 104 may include devices that reflect light at certain wavelengths and allow light at other wavelengths to pass therethrough. Decomposition or "splitting" of the conventional color image may be achieved using a "cold" mirror which allows for the image component in the visible range to be reflected towards a first image capture device (e.g., RGB CCD) 130. The remaining (NIR) component of the image passes through the "cold" mirror and is recorded by a second image capture device 132 (e.g., high sensitivity CCD array). Moreover, any of the information may be recorded and stored, e.g., electronically on a hard disk or tape library, in raw form, processed form, compressed or converted form, etc.

Appropriate filters may be used in front of each imaging/detection system to exclude some or all of the spectral components not needed for the execution of the specific task by each component. For example, an excitation attenuation filter 134 may be used to filter out laser light from the image applied to a color image capture device 130. A visible light pass filter 136 may also be used in conjunction with a color image capture device 130. For a NIR image, for example, an appropriate NIR-pass filter 138 may be used.

This technique allows for the separation of the conventional RGB image from the NIR spectral image (or any other combination of images) so that both can be acquired and displayed simultaneously. In addition, as mentioned previously, the spectral image in some approaches can be based on fluorescence or light scattering. In the latter case, the Spectral and Polarization Differential Imaging technique (SPDI) can be used to achieve depth profiling of a suspected lesion or tissue components (such as veins or arteries) providing additional diagnostic capabilities. The SPDI image can be acquired through an additional imaging module that employs simultaneous acquisition of light scattering images at different wavelengths. SPDI imaging may require additional illumination wavelengths/sources and filters as has been described in U.S. Pat. No. 7,257,437 to Stavros et al., which has been incorporated by reference.

For tumor margin delineation (or other applications where higher spatial resolution images are needed), regions of interest (suspected cancer) may be examined at the microscopic level to visualize tissue microstructure (organization and cell characteristics) using autofluorescence imaging under UV excitation. These approaches have been described in U.S. patent application Ser. No. 11/292,406 "Hyperspectral microscope for in vivo imaging of microstructures and cells in tissues", filed on Nov. 30, 2005, and which is herein incorporated by reference. This approach can be integrated into the system design described here. Implementation of such approach may include endoscopes that have zoom capabilities or utilization of more than one endoscope, each providing the desired spatial resolution.

To achieve a high level of specificity, imaging/screening using multiple optical modalities/techniques may be employed. To address this problem, one embodiment has built-in multimodal and multispectral imaging capabilities for both, the macro- and micro-scopic imaging modes. For example, for the macroscopic imaging module, imaging at different parts of the NIR spectrum can be utilized while the excitation (used for autofluorescence or contrast agent fluorescence imaging) may be at any (or multiple) wavelengths shorter than about 670-nm. Multimodal imaging can also be used in the microscopic imaging module. For example, excitation around 270-nm provides images based on tryptophan emission while excitation around 330-nm provides images based on collagen or NADH which can be separated out by selecting the appropriate spectral window for imaging (centered at 390-nm for collagen and 470-nm for NADH). These images can be acquired simultaneously (e.g. 266-nm excitation and 300-330-nm emission for tryptophan along with 355-nm excitation and 370-410 nm emission for collagen and 430-520-nm emission for NADH). In addition, the spectral range for excitation may be expanded in the visible to acquire images based on emission by other tissue fluorophores (such as Flavins and Porphyrins) or contrast agents. A schematic layout of a system according to one embodiment that incorporates RGB color imaging, NIR fluorescence imaging, SPDI imaging and three different modes of microscopic imaging (e.g., as described above) is shown in FIG. 2.

Figure 2:
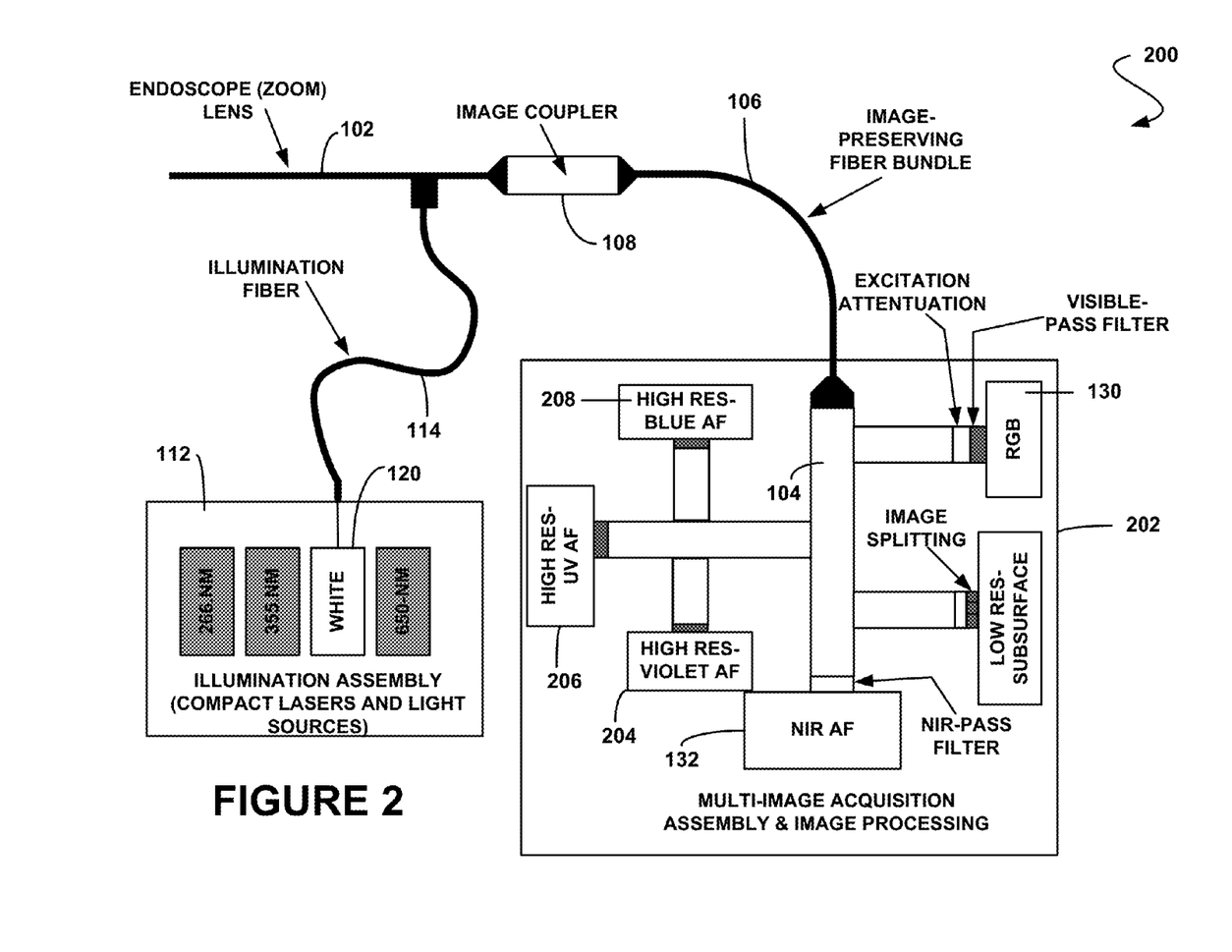
FIG. 2 illustrates a system for simultaneous acquisition of images using different techniques according to one embodiment.

Referring to the illustrative embodiment 200 of FIG. 2, similar general components as in the system 100 of FIG. 1 are used. Again, a commercially available endoscope (possibly with zoom capabilities) or other type of image forming device 102 can be used for multi-image acquisition. The endoscope is used to form and relay the images of interior body organs (esophagus, bladder, colon, etc.) and/or tissues into an image preserving fiber bundle 106. The image is then transferred into the image processing unit 202 where it is split to individual components (imaging modes) such as conventional color (RGB), SPDI (low resolution subsurface), fluorescence (low resolution autofluorescence or contrast agent) and three microscopic images in the blue, violet and ultraviolet spectrum. All images can be acquired simultaneously via image capture devices 130, 132, 204, 206, 208 and displayed separately and/or fused into composite images via software or hardware, etc.

As in the systems of FIG. 1, appropriate filters may be used in front of each imaging/detection system to exclude some or all of the spectral components not needed for the execution of the specific task by each component.

Figure 3:
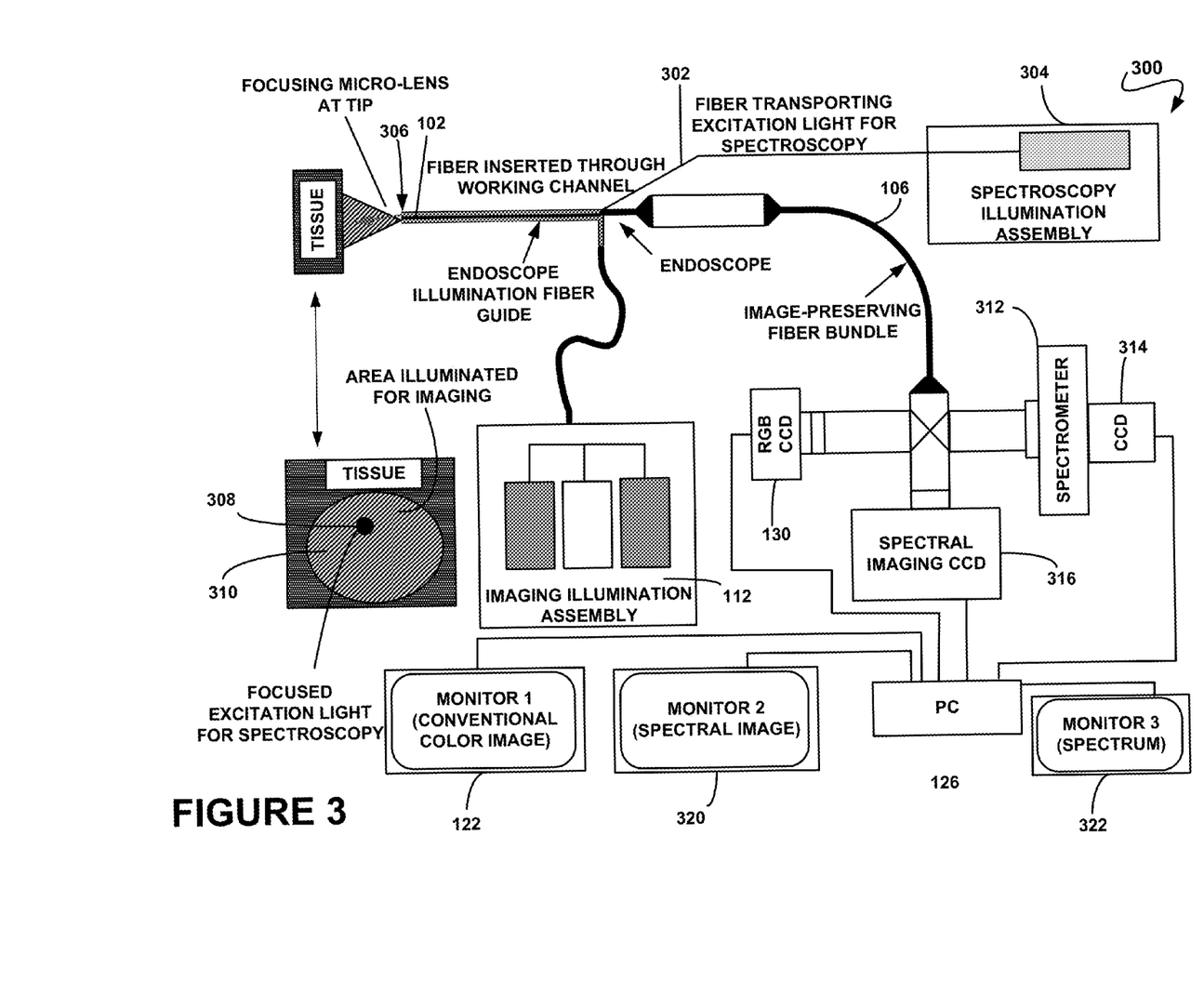
FIG. 3 illustrates a system for simultaneous acquisition of images using different techniques according to one embodiment.

The imaging approaches described above can be complemented by the acquisition of the spectrum from a single smaller region within the imaged area. One illustrative system 300 having this type of instrumentation is shown in FIG. 3, which shows a design for the simultaneous acquisition of a spectral image (such as NIR autofluorescence or contrast agent emission) along with a color RGB image that are complemented by acquisition of the spectral profile (such as Raman scattering) from a smaller area. The execution of this type of measurement that involves simultaneous acquisition of images and spectral profiles from a single point involves a number of modification/addition to the designs previously described. First, the excitation light (laser) to be used for spectroscopy is preferably delivered by a separate illumination channel 302 such as a fiber that is passed from a second illumination assembly 304 and through the working channel of the image forming device 102, e.g., endoscope, to reach the target area. A microlens 306 (such as a grin lens) located at the tip of the fiber is used to focus the light into a small area (point-like) 308 within the imaged area 310 (which may be illuminated using the endoscope's illumination channel or through a separate illumination guide external or internal to the endoscope). The spectrum (e.g., fluorescence, Raman scattering, etc.) is collected by the image forming system (lens or endoscope) and preferably projected into a specific set of fibers in the image transfer line 106, e.g., image preserving fiber bundle, that correspond to the area 308 of the image that is illuminated by the focused excitation source. At the distal end of the image preserving fiber 106, the image may be split again similarly to the way it was described above, but part of the image containing the spectral region where the spectral profile is located is directed into the slit of a spectrograph 312. The part of the image that does not contain the spectral information (not illuminated by the focused light source) may be discarded via the use of a device (such as a pinhole) that allows for spatial selection of the signal from a specific area of the image prior to entering the slit (or equivalent apparatus such a pinhole or input fiber) of the spectrometer 312. The spectrum may be spectrally resolved and recorded by an appropriate device 314 (such as a CCD). Another spectral imaging device 316 may acquire a different spectral image (such as NIR autofluorescence or contrast agent emission) while a color image capture device 130 captures a color RGB image. As above, representations of the various images can be displayed on monitors 122, 320, 322; processed by a computing device 126; superimposed on one another; etc. Note that the information output relating to the spectral profile from the smaller area may be representative data showing some computed result based on the spectral image received.

As an example of possible implementation of the system shown in FIG. 3, the specific spectral ranges used by each modality may be the following: 1) The RGB image is obtained using white light illumination in the 400-650 nm spectral range. 2) The NIR autofluorescence or contrast agent emission image is obtained under 650 nm excitation and emission in the 680-790 nm spectral range. 3) To record the Raman scattering spectrum from a specific location within the imaged area, laser excitation at 800-nm is utilized while the Raman scattering spectrum of the tissue extends from 810-950 nm.

As in the systems of FIGS. 1 and 2, appropriate filters may be used in front of each imaging/detection system to exclude all other spectral components except the one needed for the execution of the specific task by each component.

Figure 4:
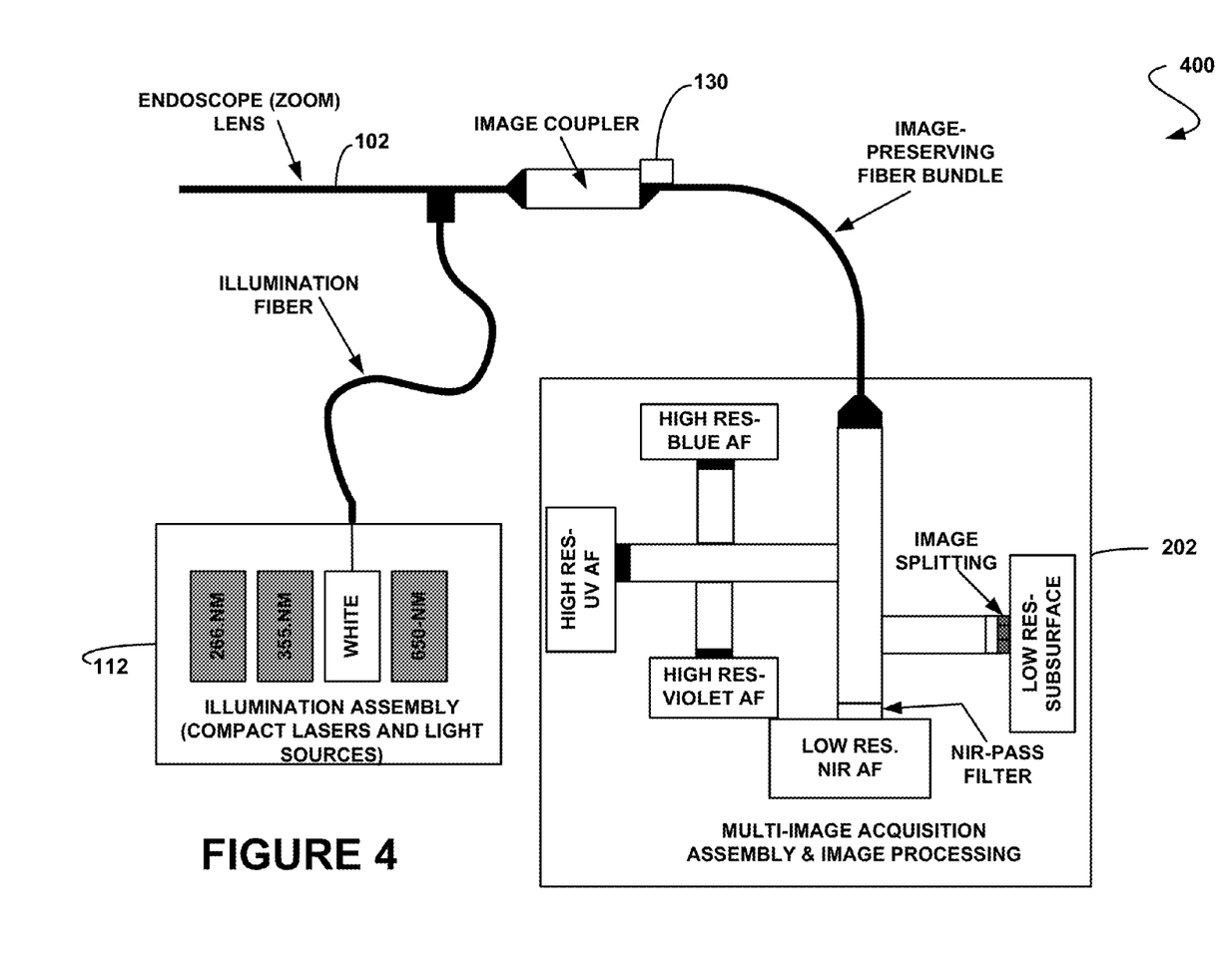
FIG. 4 illustrates a system for simultaneous acquisition of images using different techniques according to one embodiment.

FIG. 4 depicts yet another illustrative embodiment 400 in which an image is captured nearer to the image forming device 102. Accordingly, an image capture device may be coupled to the image forming device 102, the image transfer module 108, a first splitter, etc. In the approach shown, a RGB CCD 130 is coupled to the image transfer module 108. The color image is split from the remaining image at the image transfer module 108, and the remaining image passes through the image transport line 106 to another image capture device and/or image processing unit 202. Typically, the resolution of the recorded image formed by the image forming device 102 is dependent upon the number of fibers in a fiber bundle of the image transfer line 106. This approach, for instance, more readily allows capture of a higher resolution color image and lower resolution NIR image through a fiber bundle.

The embodiments described herein, and the many variations and permutations thereof, have many novel aspects. For instance, some embodiments include integration of different imaging modalities into a single system that can be used for in vivo screening and interrogation of tissue in a clinical setting aiming at providing sufficient information to achieve in real time a) histopathology evaluation, b) surface or subsurface tissue component visualization and separation, and c) tissue evaluation. In some embodiments, the spectral image(s) are simultaneously acquired and displayed with a conventional color (RGB) image which helps minimize the extra time for implementation of the new imaging method(s) (e.g., no need to insert a specialized endoscope) while the operator can directly correlate the spectra image or spectral profile with the images he/she is trained to utilize as the primary guidance tool.

Uses of the Embodiments

Embodiments of the present invention may be used in a wide variety of applications, and potentially any application in which imaging is useful.

Illustrative uses of various embodiments of the present invention include, but are not limited to detection and diagnosis of disease, cancer detection and imaging, detection and imaging of other tissue pathologies, detection and analysis of cellular processes, microscopy, multi-spectral and hyperspectral imaging, separation and imaging of tissue components, endoscopy and interior body imaging, remote sensing and imaging, etc.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A system, comprising:
an image forming device for forming an image of an area of interest;
an illumination device for illuminating the area of interest with light containing multiple components, wherein the illumination device is within the image forming device;
an illumination channel and a lens for focusing light from the illumination channel onto a smaller portion of the area of interest than that illuminated by the illumination device,
wherein the image forming device is configured to form a macroscopic image from the area of interest and to form a microscopic image from the smaller portion of the area of interest,
wherein the microscopic image and macroscopic images are formed simultaneously;
at least three light sources coupled to the illumination device and providing light to the illumination device containing different components, each component having distinct spectral characteristics and relative intensity;
an image transfer line for transferring the image from the image forming device to an image analyzer, wherein the image transfer line is flexible for allowing articulation of the image forming device relative to the image analyzer;
the image analyzer comprising at least two devices that reflect light at predefined wavelengths and allow light at other wavelengths to pass therethrough,
wherein each of the at least two devices simultaneously receives the image formed by the image forming device from the image transfer line thereby simultaneously splitting the image formed by the image forming device into multiple discrete component parts based on type of imaging,
the image analyzer being configured to output the multiple discrete component parts of the image; and
at least three image capture devices, each image capture device being configured to capture one of the discrete component parts of the image, the image capture devices being configured to capture the discrete component parts simultaneously and independently from the other image capture devices,
wherein each image capture device is configured to independently and simultaneously with the other image capture devices output image information based on the discrete component part captured thereby to a respective output device coupled thereto.

2. The system of claim 1, wherein the image forming device includes an endoscope-type device used in the medical field to view interior body structures.

3. The system of claim 1, the image transfer line is a fiber optic bundle for transferring the image from the image forming device to the image analyzer,
wherein the image received at the image analyzer is the image formed from the image forming device,
wherein two of the at least two devices of the image analyzer are positioned to simultaneously receive the image from the image transfer line prior to the image being split.

4. The system of claim 1, wherein the illumination device is integral to the image forming device.

5. The system of claim 1, wherein one of the at least three light sources includes a narrow band light source configured to provide narrow band excitation at 800 nm for emission in the spectral range of 800-1000 nm and a second of the at least three light sources provides excitation under 650 nm for emission in a spectral range of 680-790 nm.

6. The system of claim 1, further comprising the output devices for displaying information based on the outputs of the image capture devices capturing the discrete component parts simultaneously.

7. The system of claim 1, the system is configured to output composite image information based on at least two discrete component parts of the image.

8. The system of claim 1,
wherein a spectrum reflected from the smaller portion of the area of interest is projected into a specific set of fibers in the image transfer line that correspond to the smaller portion of the area of interest that is illuminated by the focused light.

9. The system of claim 1, further comprising
an illumination channel and a lens for focusing light from the illumination channel onto a smaller portion of the area of interest than that illuminated by the illumination device; and
a spectrometer for receiving reflected light originating in the illumination channel.

10. A method, comprising:
illuminating, utilizing an illumination device, an area of interest with at least three light sources, at least one of the light sources including a white light source emitting light in a visible spectrum, wherein the illumination device is within an image forming device;
focusing light from an illumination channel onto a smaller portion of the area of interest than that illuminated by the illumination device,
wherein the image forming device forms a macroscopic image from the area of interest and forms a microscopic image from the smaller portion of the area of interest;
receiving an image from the image forming device through an image transfer line for transferring the image from the image forming device to an image analyzer, the image being based on the illuminated area of interest, wherein the image transfer line is flexible for allowing articulation of the image forming device relative to the image analyzer;
simultaneously splitting, using at least two devices of the image analyzer, the image formed by the image forming device into multiple discrete component parts based on type of imaging, wherein the at least two devices of the image analyzer are positioned to simultaneously receive the image from the image transfer line prior to the image being split;
capturing the discrete component parts of the image simultaneously by at least three image capture devices; and
outputting image information simultaneously based on the discrete component parts captured thereby to a respective output device coupled thereto.

11. The method of claim 10, wherein the image forming device includes an endoscope-type device used in the medical field to view interior body structures.

12. The method of claim 10, wherein one of the at least three light sources includes a narrow band light source configured to provide narrow band excitation at 800 nm for emission in the spectral range of 800-1000 nm, and a second of the at least three light sources provides excitation under 650 nm for emission in a spectral range of 680-790 nm.

13. The method of claim 10,
wherein the microscopic image and macroscopic images are formed simultaneously.

14. The method of claim 13, further comprising a spectrometer for receiving reflected light originating in the illumination channel.

15. The method of claim 10, wherein composite image information based on at least two discrete component parts of the image is output, wherein a first filter is positioned between the image analyzer and a first of the image capture devices; and a second filter is positioned between the image analyzer and a second of the image capture devices.

16. The system of claim 7, wherein the output composite image information includes an overlying image that includes only portions of a source image that have an intensity above a threshold value.

17. The system of claim 1, wherein at least three of the multiple discrete component parts include a plurality of different simultaneous image components, wherein the image components are selected from a group consisting of: a color image, a fluorescent image, a light scattering image, and a plurality of microscopic images at different parts of a spectrum.

18. The system of claim 3, wherein the image transfer line is selected from a group consisting of: an image preserving fiber, a fiber bundle, a conduit, a channel having refractive portions, and a channel having reflective portions.

19. The method of claim 10,
wherein at least three of the discrete component parts include a plurality of different simultaneous image components,
wherein the image components are selected from a group consisting of: a color image, a fluorescent image, a light scattering image, and a plurality of microscopic images at different parts of a spectrum.

20. A system, comprising:
an image forming device for forming an image from an area of interest, wherein the image forming device is in an endoscope;
wherein the image forming device comprises an illumination channel and a lens for focusing light from the illumination channel onto a smaller portion of the area of interest than that illuminated by the illumination device,
wherein the image forming device is configured to form a macroscopic image from the area of interest and to form a microscopic image from the smaller portion of the area of interest, wherein the microscopic image and macroscopic images are formed simultaneously;
an illumination device for illuminating the area of interest with light containing multiple components, wherein the illumination device is within the image forming device;
at least three light sources coupled to the illumination device and providing light to the illumination device containing different components, each component having distinct spectral characteristics and relative intensity, wherein the at least three light sources include at least one light source selected from the group consisting of: a white light source emitting light in a visible spectrum, a laser light source, and another light source providing light to the illumination device;
an image transfer module interfaced with the image forming device to assist in coupling the formed image to an image transfer line;
the image transfer line for transferring the image from the image forming device to an image analyzer, wherein the image transfer line is flexible for allowing articulation of the image forming device relative to the image analyzer, wherein the image transfer line includes an image preserving fiber bundle;
the image analyzer coupled to the image transfer module via the image transfer line, the image analyzer comprising at least two devices that reflect light at predefined wavelengths and allow light at other wavelengths to pass therethrough,
wherein each of the at least two devices simultaneously receives the image formed by the image forming device from the image transfer line thereby simultaneously splitting the image formed by the image forming device into multiple discrete component parts based on type of imaging, the image analyzer being configured to output the multiple discrete component parts of the image,
wherein two of the at least two devices of the image analyzer are positioned to simultaneously receive the image from the image transfer line prior to the image being split; and
at least three image capture devices, each image capture device being configured to capture one of the discrete component parts of the image,
at least one of the image capture devices being configured with a spectrophotometer for receiving reflected light originating in the illumination channel to capture a spectral profile from the smaller portion of the area of interest,
the image capture devices being configured to capture the component parts simultaneously and independently from the other image capture devices,
wherein a first filter is positioned between the image analyzer and a first of the image capture devices; and a second filter is positioned between the image analyzer and a second of the image capture devices,
wherein each image capture device is configured to independently and simultaneously with the other image capture devices output image information based on the discrete component part captured thereby to a respective output device coupled thereto,
wherein the system is configured to fuse the simultaneously output image information into a composite image and output the composite image information to another output device,
wherein a spectrum reflected from the smaller portion of the area of interest is projected into a specific set of fibers in the image transfer line that correspond to the smaller portion of the area of interest that is illuminated by the focused light from the illumination channel.

21. The system of claim 1, wherein the system is configured to fuse the simultaneously output image information into a composite image and output the composite image information to another output device.

22. The method of claim 10, comprising fusing the image information into a composite image, wherein the composite image is output to another output device simultaneously with the image information simultaneously output by the image capture devices.

23. The system of claim 1, comprising a first filter positioned between the image analyzer and a first of the image capture devices; and a second filter positioned between the image analyzer and a second of the image capture devices.

24. The system of claim 20, wherein the output composite image information includes an overlying image that includes only portions of a source image that have an intensity above a threshold value.

* * * * *